US00PP34613P3

(12) United States Plant Patent
Olesen et al.

(10) Patent No.: US PP34,613 P3
(45) Date of Patent: Sep. 27, 2022

(54) ***CLEMATIS* PLANT NAMED 'EVIPO114'**

(50) Latin Name: *Clematis viticella*
Varietal Denomination: Evipo114

(71) Applicants: Mogens Nyegaard Olesen, Fredensborg (DK); Raymond J Evison, Guernsey (GB)

(72) Inventors: Mogens Nyegaard Olesen, Fredensborg (DK); Raymond J Evison, Guernsey (GB)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,637

(22) Filed: Sep. 7, 2021

(65) Prior Publication Data

US 2022/0095520 P1 Mar. 24, 2022

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 5/02; A01H 5/00
See application file for complete search history.

(56) References Cited

PUBLICATIONS https://www.raymondevisonclematis.com/products/vicki; Oct. 23, 2021; 2 pages.*
https://horticultureconnected.ie/news/events-news/plantarium/novelties-plantarium-2019/; Aug. 6, 2019; 2 pages.*

* cited by examiner

*Primary Examiner* — Kent L Bell

(57) ABSTRACT

A new *Clematis* plant with a compact growth habit, profuse, red-purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification:
Genus: *Clematis.*
Species: *viticella.*
Variety denomination: 'Evipo114'.

This application claims priority to Plant Breeder's Rights Application Number 2020/2282, which was filed at the Community Plant Variety Rights Office in the European Union on Sep. 21, 2020, the contents of which are hereby incorporated by reference for all purposes.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2007 and the resulting seeds were planted the following winter in a controlled environment in Guernsey, Channel Islands, United Kingdom. The new variety named 'Evipo114' originated as a single seedling from the stated cross.

The new *Clematis* plant may be distinguished from its female seed parent and male pollen parent by the following characteristics. The female seed parent has a growth height of 100 cm in one season, while the new variety grows to 70 cm in a single growing season. The male seed parent has light pink tepals while the new variety has red-purple tepals.

The objective of the hybridization of this *Clematis* plant was to create a new and distinct variety for nursery culture with unique qualities such as:

1. Uniform and abundant red-purple flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo114' was selected by Mogens N. Olesen and Raymond J. Evison in their *Clematis* development program in the Channel Islands, United Kingdom in 2008. Asexual reproduction of 'Evipo114' by means of vegetative stem cuttings was first performed by Mogens N. Olesen and Raymond J. Evison in the nursery during the summer of 2008. This initial and subsequent asexual propagations have demonstrated that the characteristics of 'Evipo114' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo114'.

Specifically illustrated in FIG. 1 of the drawings are flowers at various stages of opening, flowers with tepals detached revealing reproductive flower parts, and a flower bud.

DETAILED DESCRIPTION OF THE VARIETY

Figure 1:
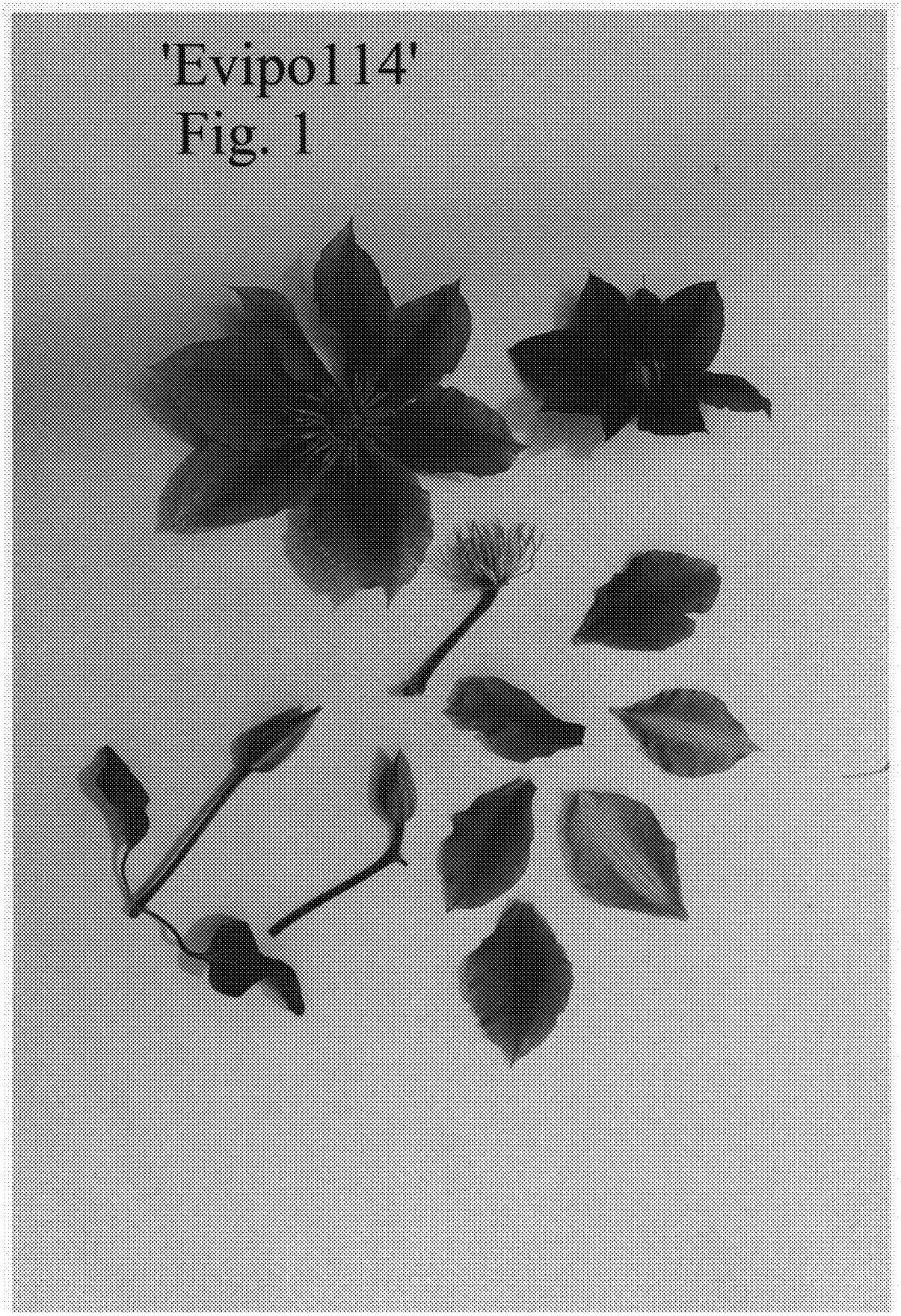
Figure 2:
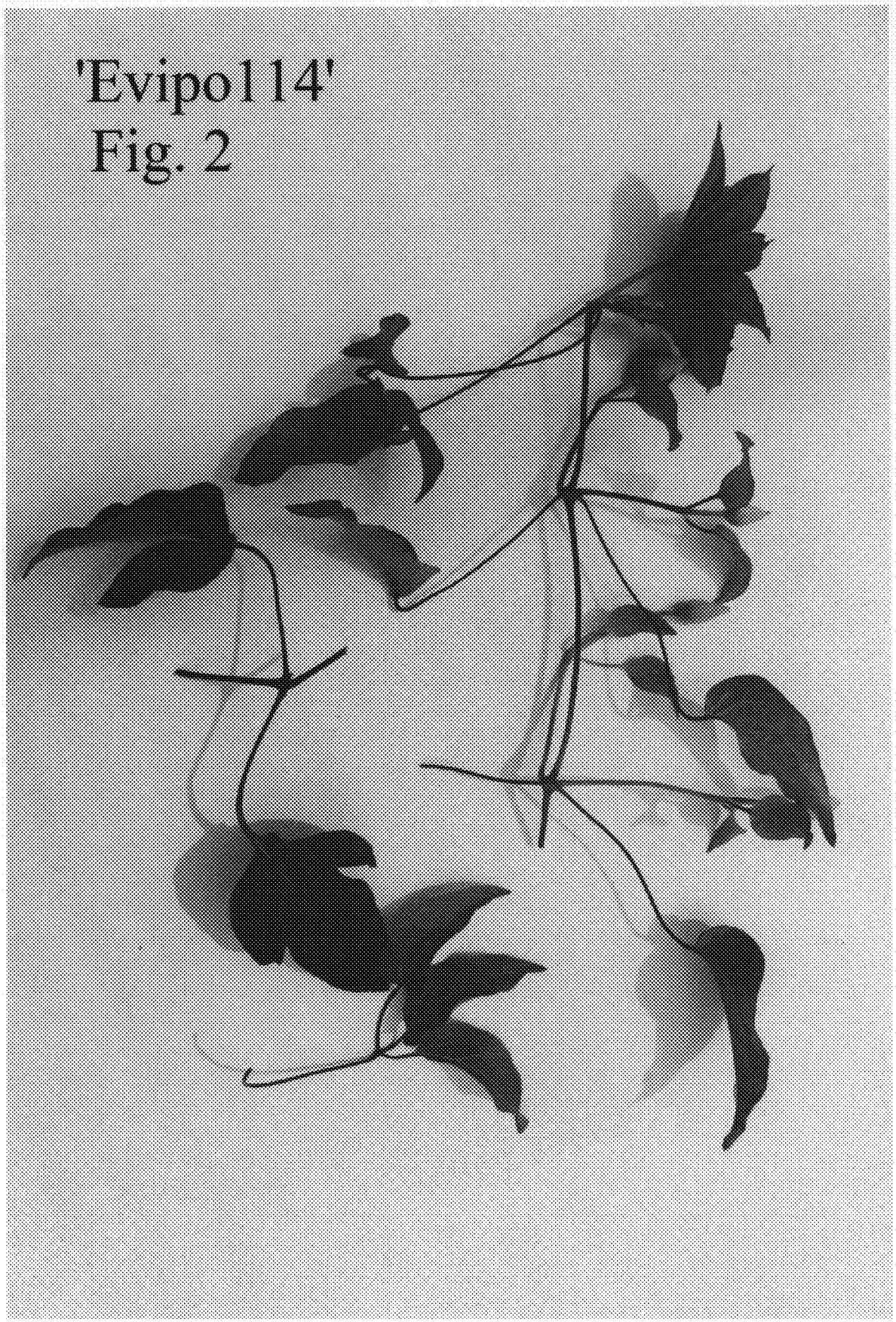
FIG. 2 shows a flowering branch, leaves and stems. Illustrated plants are 2 years of age.

The following is a detailed description of 'Evipo114', as observed in its growth throughout the flowering period in Odense Denmark. Observed plants were cultivated for a period of 24 months and brought to flower in 24 cm containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo043' described and illustrated in U.S. Plant patent application Ser. No. 13/986,919, now abandoned, are compared to 'Evipo114' in Chart 1.

CHART 1

| | 'Evipo114' | 'Evipo043' |
|---|---|---|
| Flower diameter | 123 mm | 120 mm |
| Tepal upper surface after opening | Purple Group 64A | Red-Purple Group 71A |

FLOWER AND FLOWER BUD

Blooming habit: Continuous. The natural flowering period is generally from July to September.

Flower bud:

*Size*.—Normally 29 mm in length. Bud diameter is 11 mm.

*Bud form*.—Long campanulate, broad based.

*Bud color*.—Yellow-Green Group 144A and Yellow-Green Group 145C.

*Texture*.—Pubescent.

Pedicel:

*Surface texture*.—Pubescent.

*Length*.—On average 54 mm in length with 2 mm diameter.

*Color*.—Yellow-Green Group 144A.

*Strength*.—Moderately strong.

Receptacle:

*Surface texture*.—Lightly pubescent.

*Shape*.—Broad funnel.

*Size*.—1.5 mm (h)×4 mm (w).

*Color*.—Yellow-Green Group 144A.

Flower arrangement:

*Location on vine*.—New and old growth.

*Borne*.—Flowers occur at each axillary bud along the branch.

Flower bloom:

*Size*.—On average, flowers are 123 mm in diameter and 20 mm in depth.

*Profile*.—Open flowers are nearly flat.

*Fragrance*.—None.

*Lasting quality*.—Flowers normally remain up to 10 days on the plant.

Tepals:

*Tepal color*.—Upon opening, the upper surface is Purple Group 64A. As flowers mature the upper surface color changes to Purple Group 76A with a distinct central bar color Red-Purple Group 70A. The lower surface has a central bar of Yellow-Green Group 144B. Purple Group 76A next to the central bar. At the margins Purple Group N77B. After opening the lower surface changes to Purple Group 76B, and marginal intonations of Violet Group 84B with a central bar of White Group 155 B.

*Quantity*.—Normally 7 tepals.

*Size*.—Tepals are 56 mm in length by 32 mm wide.

*Shape*.—Individual tepal shape is ovate. The tepal apex is acuminate. The tepal base is acute.

*Apex recurvature*.—None.

*Tepal cross section*.—Flat.

*Margins*.—Entire. Moderate undulations of margin observed.

*Persistence*.—Tepals drop off cleanly.

Reproductive organs:

*Pollen*.—None observed.

*Anthers*.—Size: 6 mm in length. Color: Yellow Group 8C. Quantity: On average, 27.

*Filaments*.—Color: White Group 155A. Length: 12 mm.

*Pistils*.—Quantity: On average, 19.

*Styles*.—Color: Green-White Group 157 C. Length: 15 mm.

*Stigmas*.—Relative to the position and length of the anthers, stigmas are beneath or inferior.

Seed head characteristics: Seed not observed to date.

PLANT

Plant form: Climbing by way of petioles.

Plant growth: Compact.

Size: Seasons growth attains 70 cm in height. Average spread is 50 cm. Flowering begins at 20 cm from the base of the plant.

Stems:

*Color*.—Juvenile stems are Yellow-Green Group 144A. Mature stems are Greyed-Orange Group 177A and Brown Group 200A.

*Internodes*.—On average, 60 cm between nodes.

*Diameter*.—About 2 mm.

*Texture*.—Mature stems are ribbed.

Plant foliage:

*Leaf characteristics*.—Deciduous.

*Arrangement*.—Both simple and trifoliate.

*Leaf size*.—Compound trifoliate leaves are leaves are about 110 mm (l)×65 mm (w). Simple leaves are about 71 mm (l)×48 mm (w). On trifoliate leaves terminal leaflets are 50 mm(l)×31 mm (w).

*Abundance*.—On average 1 or 2 leaves per 10 cm of stem.

*Leaf color*.—Juvenile upper Yellow-Green Group 144B with marginal intonations of Greyed-Purple Group 187B. Juvenile lower Yellow-Green Group 144B. Mature upper Yellow-Green Group 147A. Mature lower Yellow-Green Group 146A.

*Stipules*.—Absent.

*Petioles*.—Size: Normally 70 mm in length by 1 mm diameter. Texture: Smooth. Color: Greyed-Purple Group 183A.

*Petioloule*.—Size: About 10 mm in length by 1 mm diameter. Texture: Smooth. Color: Greyed-Purple Group 183A.

*Leaflet shape*.—Acuminate. The base is rounded or oblique. The apex acute.

*Margin*.—Trifoliate leaves are entire. Simple leaves have three lobes.

*Surface*.—The upper side is smooth, the lower side is smooth.

*Thickness*.—Moderate.

*Glossiness*.—Moderately glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo114', substantially as described and illustrated herein.

* * * * *

'Evipo114'

'Evipo114'